United States Patent
Hedges, Jr. et al.

[11] Patent Number: 5,814,030
[45] Date of Patent: Sep. 29, 1998

[54] PRE-STERILIZED, DISPOSABLE, OPHTHALMIC IRRIGATION DEVICE

[76] Inventors: Thomas R. Hedges, Jr., 245 Nicholson Dr., Moorestown, N.J. 08057; David Jaspan, 105 Spring House Ct., Cherry Hill, N.J. 08002

[21] Appl. No.: 757,373

[22] Filed: Nov. 27, 1996

Related U.S. Application Data

[63] Continuation-in-part of Ser. No. 373,580, Jan. 17, 1995, abandoned.

[51] Int. Cl.$^6$ .................................................. A61M 35/00
[52] U.S. Cl. ............................................................ 604/294
[58] Field of Search ................................. 604/19, 36, 42, 604/80, 289, 294, 408, 411, 415, 412; 606/4–6; 359/809, 810

[56] References Cited

U.S. PATENT DOCUMENTS

| | | | |
|---|---|---|---|
| 4,654,026 | 3/1987 | Underwood | 604/80 |
| 4,734,091 | 3/1988 | Boyle et al. | 604/294 |
| 4,798,599 | 1/1989 | Thomas | 604/19 |
| 5,066,276 | 11/1991 | Wang | 604/294 |
| 5,242,392 | 9/1993 | Vaughn | 604/80 |
| 5,387,201 | 2/1995 | Fowler | 604/294 |
| 5,545,153 | 8/1996 | Grinblat et al. | 604/294 |
| 5,599,303 | 2/1997 | Melker et al. | 604/80 |

*Primary Examiner*—Mark O. Polutta
*Assistant Examiner*—David J. Cho
*Attorney, Agent, or Firm*—Beehler & Pavitt; Norton Townsley

[57] ABSTRACT

The present invention is a corneal irrigation device which can attach to many different models and makes of microscopes, provides a steady mount for the delivery system, and is provided as a pre-sterilized kit. The heart of this invention is its ball socket filter straw delivery unit. This sub-assembly comprises a ball with a diametrical hole. Through this hole is affixed a filter straw or cannula preferably with a slight curvature to it. The ball and cannula assembly is supported and retained by a ring which has a spherical inner surface closely matching the shape of the ball. When snapped into the ring, the ball can be hand rotated to that the lower end of the cannula can be pointed to any point contained within a large distance around the ball. However, once rotated to a desired position, frictional forces between the ball and ring keep the ball stationary. The delivery unit is affixed to a very solid bracket which includes a flat, vertical surface. This surface is provided with a layer of semi-permanent adhesive which is adhered to a microscope. The upper end of the cannula is attached to a length of tubing which is inserted into a standard saline bag hanging from an IV pole.

10 Claims, 4 Drawing Sheets

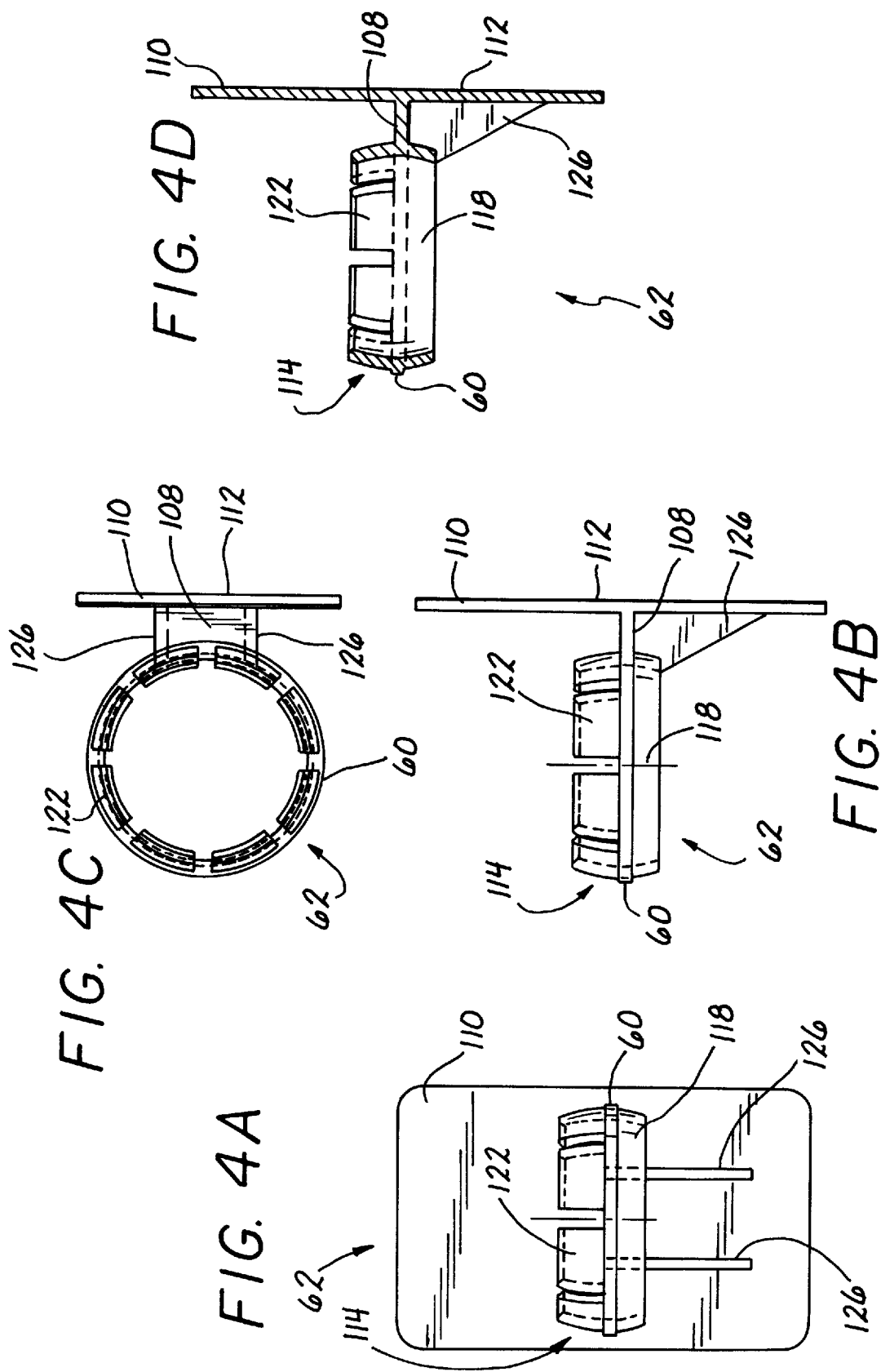

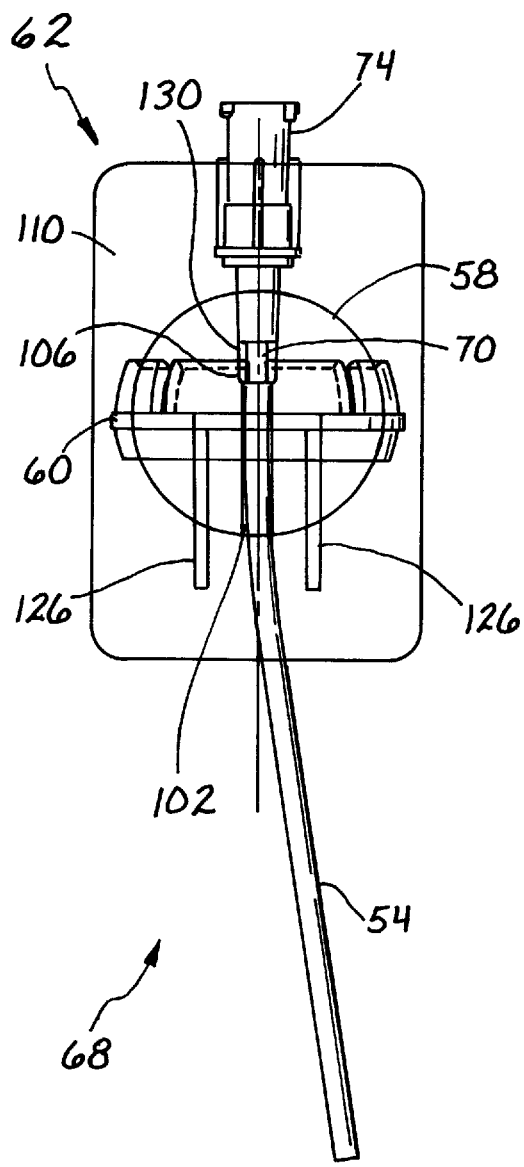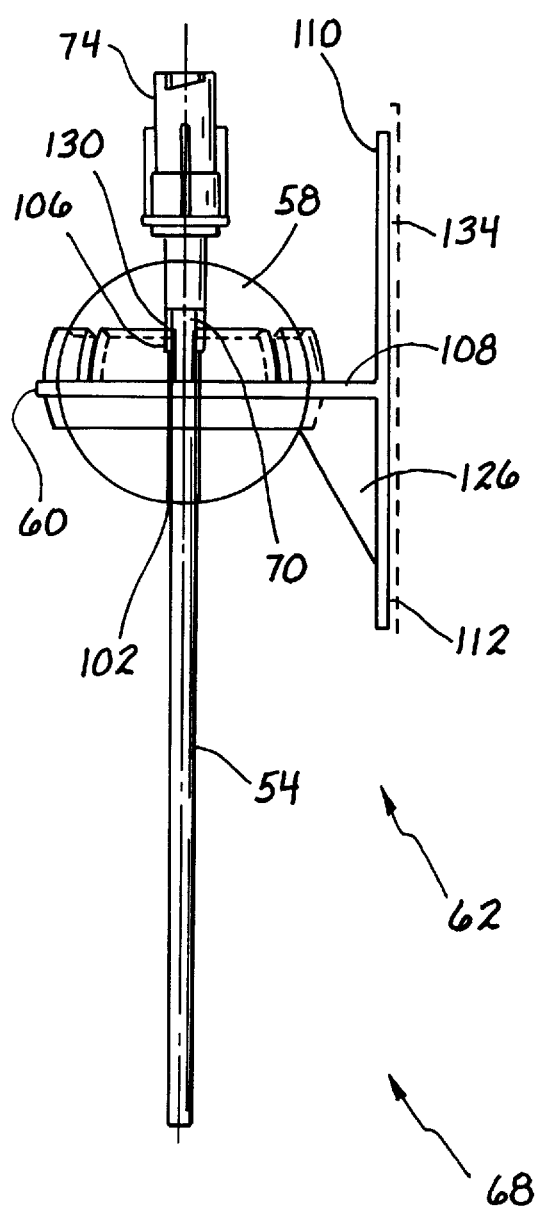
FIG. 5A
FIG. 5B

PRE-STERILIZED, DISPOSABLE, OPHTHALMIC IRRIGATION DEVICE

This application is a continuation in part of application Ser. No. 08/373,580 filed Jan. 17, 1995 now abandoned.

BACKGROUND OF THE INVENTION

The present invention relates to the field of irrigation of corneas during eye surgery and more particularly to irrigation that is dispensed from a cannula attached to the microscope that is used during such surgery.

Eye surgery is carried out with the aid of an operating microscope. Because enormous damage can be done if probes are only millimeters off, the surgeon must have a clear field of view and a clear image of the patient's cornea during surgery. During surgery, the patient's eye is held open and surgery is conducted through incisions adjacent to the cornea. Consequently, it is possible for blood and other fluids to accumulate on the cornea but also, of greatest importance, is that the cornea tends to dry out. As the cornea dries or an oily tear film accumulates, the surgeon's view becomes clouded. Then, there is danger of misplacing a probe and doing severe damage to the eye.

Currently the only means of wetting the cornea and removing blood and other tissue is for the surgeon to have an assistant with a hand held squeeze bottle of balanced salt solution (BSS) irrigate the cornea. This only approximates a satisfactory method of irrigation. The surgeon must constantly tell the assistant exactly where to direct the fluid flow and from what angle. Further the fluid pressure and interval of irrigation are uncontrolled so that irrigation results desired by the surgeon are difficult to achieve.

A device known as a Drews Microscope Dripper was published about 30 years ago. It has a stainless steel ring designed to be screwed on to the 50 mm objective lens of a Zeiss microscope. Attached to the ring via a flexible attachment mechanism is a metal cannula, which can be directed towards the cornea. By attaching the cannula to a drip bottle via a stopcock, the cornea can be irrigated by gravity feed during surgery. Using this crude device the surgeon is unable to adequately control the irrigation. Also, any tugging on the supply tubing displaces the cannula. Further, the device only fits onto one lens of one microscope and must be sterilized prior to each operation. These days, surgical teams much prefer pre-sterilized, disposable surgical devices.

Development of a corneal irrigation device which can attach to many different models and makes of microscopes, provides a steady mount for the delivery system, and is provided as a pre-sterilized kit represents a great improvement in the field of ophthalmic surgery and satisfies a long felt need of the eye surgeon.

SUMMARY OF THE INVENTION

The present invention is a corneal irrigation device which can attach to many different models and makes of microscopes, provides a steady mount for the delivery system, and is provided as a pre-sterilized kit. The heart of this invention is its ball socket filter straw delivery unit. This unit comprises a ball with a diametrical hole. Through this hole is affixed a filter straw or cannula preferably with a slight curvature to it. The ball and cannula assembly is supported and retained by a ring which has a spherical inner surface identical to the shape of the ball. The ring has superior castellations and is sized to fit approximately around the equator of the ball. When the ball is snapped into the ring, the ball can be hand rotated so that the lower end of the cannula can be directed to any point under the ball and within a large distance around the ball. However, once rotated to a desired position, frictional forces between the ball and ring keep the ball stationary.

The delivery unit is affixed to a very solid bracket which includes a flat, vertical surface. This surface is provided with a layer of semi-permanent adhesive. Consequently, the bracket can be adhered to a microscope for use during surgery and peeled off after surgery is completed. Since the delivery unit has a large reach, the bracket can be attached to the side of even large microscopes and the end of the cannula can still be pointed to any desired point in the surgical arena.

The upper end of the cannula is provided with a standard, luer slip fitting. The fitting is attached to a length of tubing which has a standard spike fitting at its upper end. The spike fitting can then be inserted into a standard saline bag hanging from an IV pole.

This invention is provided as a pre-sterilized kit. Pouches containing the pre-sterilized kits along with standard bags of saline solution are provided in boxes or cartons. After surgery, the kits and used bags are discarded.

An appreciation of the other aims and objectives of the present invention and an understanding of it may be achieved by referring to the accompanying drawings and description of a preferred embodiment.

BRIEF DESCRIPTION OF THE DRAWINGS

FIG. 4A is a front view of the integral ring and support bracket.

FIG. 4B is a side view of the integral ring and support bracket.

FIG. 4C is a top view of the integral ring and support bracket.

FIG. 4D is a side, cross section of the integral ring and support bracket.

FIG. 5A is a front cross section of the ball-socket filter straw delivery unit and integral support bracket.

FIG. 5B is a side cross section of the ball-socket filter straw delivery unit and integral support bracket.

DETAILED DESCRIPTION OF THE PREFERRED EMBODIMENT

Figure 1:
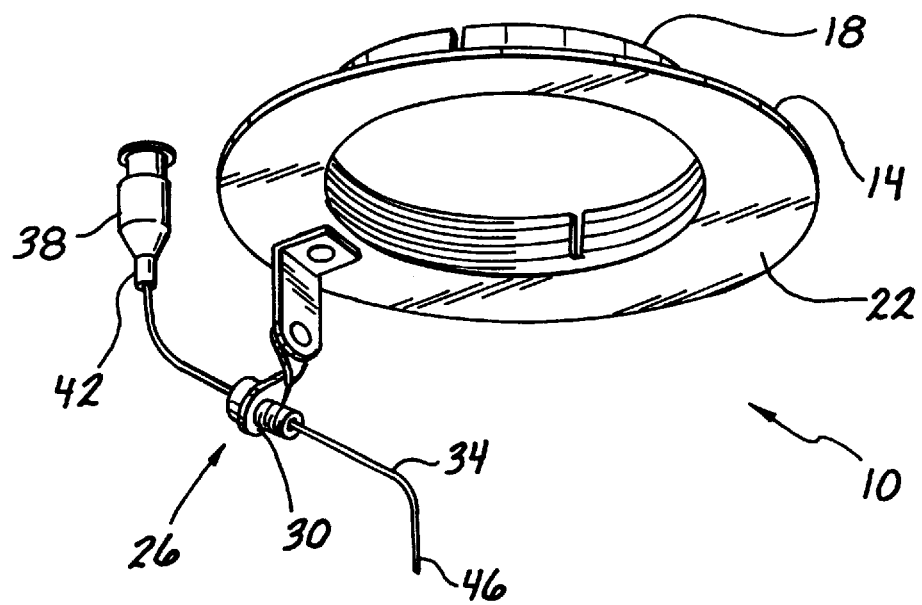
FIG. 1 is an illustration of the prior art, the Drews Microscope Dripper.

FIG. 1 is an illustration of the prior art, the Drews Microscope Dripper 10. The Drews Dripper comprises a ring 14 threaded at its upper end 18 to attach to the 50 mm objective lens of a Zeis microscope. Attached to the lower flange 22 of this ring 14 is a flimsy adjustable bracket 26. Through the outer end 30 of this bracket 26 passes a metal cannula 34 with a standard fitting 38 for attaching a supply tube at its upper end.

It will readily be appreciated that the Drews Microscope Dripper 10 suffers from a number of deficiencies:

it only fits on one lens of one microscope;
 the lower or delivery end 46 of the cannula 34 can only be adjusted to irrigate a limited portion of the surgical arena;
 it must be sterilized after each use; and
 the bracket 26 must become loose after a few uses.

Figure 2:
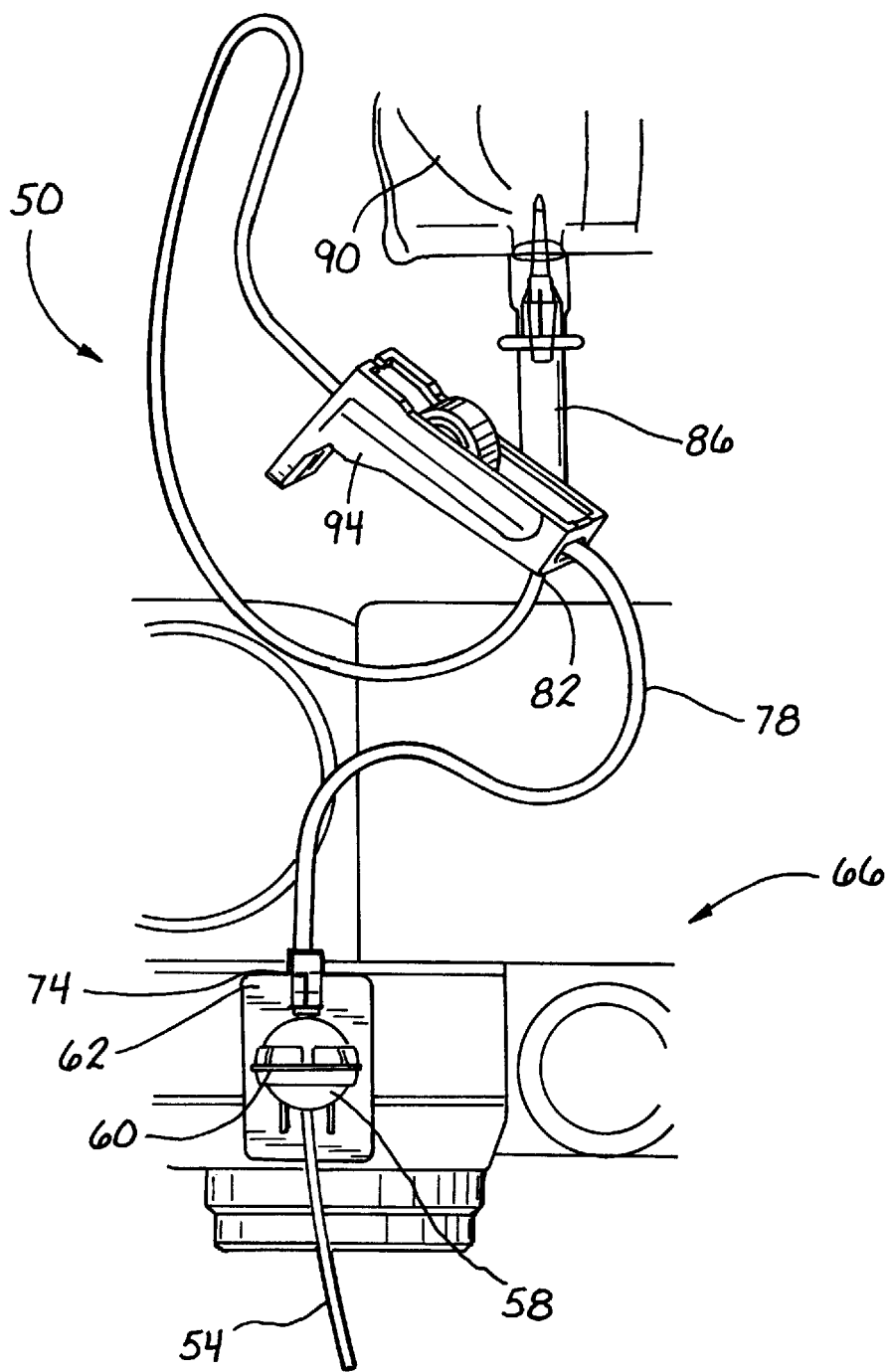
FIG. 2 shows the kit of this invention in place ready for surgery.

FIG. 2 shows this invention 50 in place ready for surgery. The invention comprises a filter straw or cannula 54 which passes through a ball 58. The cannula 54 is preferably made of plastic and has a slight curve. The ball 58 is frictionally retained in the ring portion 60 of an integral ring and bracket 62 assembly which is temporarily adhered to a microscope 66. The subassembly of the ball 58, cannula 54 and integral ring and bracket assembly 62 is called the ball-socket filter straw delivery unit 68. Attached to the top 70 (not visible in this Figure) of the cannula 54 via a standard fitting 74 is a length of supply tubing 78. A standard spike fitting 86 is attached to the top 82 of the tube 78. The spike fitting 86 inserts into a standard saline bag 90. Around the tube 78 is a device 94 for constricting the tube in order to remove air bubbles and adjust the flow rate of the saline solution. The preferred device 94 is a standard roller controller.

Figure 3:
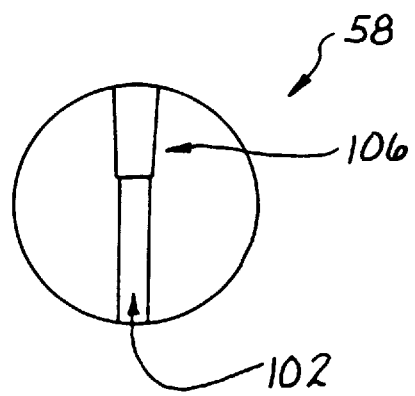
FIG. 3A is a cross section of the ball.

FIG. 3 is a cross section of the ball 58 component. The ball 58 is a precisely machined sphere, about 1 inch in diameter, preferably made of a plastic like polypropylene. Through the middle of the ball 58 is a hole 102, about 0.2 inches in diameter with a larger tapered section 106 at one end.

FIGS. 4A–4C are views of the integral ring and support bracket 62. The integral ring and support bracket 62 includes a ring portion 60 and a bracket portion 110 and a main rib 108 connecting the two. The integral ring and support bracket 62 is preferably made of a plastic such as polypropylene. The ring portion 60 and main rib 108 are at right angles to the bracket portion 110. This allows the ring portion 60 to assume an approximately horizontal position when the bracket portion 110 is mounted approximately vertically. The bracket portion 110 includes a rear-facing, flat mounting surface 112. The size of the bracket portion 110 is about 1½ inches by 2 inches.

The interior diameter of the ring portion 60 is the same as the diameter of the ball 58 and is shaped to fit approximately around the equator of the ball 58. The ring portion has an upper segment 114 which is castellated and a lower segment 118 which is continuous. The castellations 122 allow the ball 58 to be initially snapped into the ring 60. After the ball 58 is snapped into the ring 60, frictional forces between the ball 58 and the ring 60 prevent the ball 58 from moving under minimal applied force. Angled ribs 126 increase the stability of the connection of the ring portion 60 to the bracket portion 110. While FIGS. 4A–4C illustrate an integral ring and support bracket 62, that can be formed in a single mold, it will be obvious to those familiar to the art to which this invention pertains that the ring portion 60, ribs 108, 126 and bracket portion 110 could all be made as separate components and fastened together to form this sub-assembly.

FIGS. 5A and 5B are cross sections of the assembled ball socket filter straw delivery unit 68. The ball 58 is retained in the ring section 60 of the integral ring and support bracket 62. The cannula 54 passes through the hole 102 in the ball 58. The top end 70 of the cannula is fastened to a standard fitting 74. The nose 130 of this fitting 74 fits snugly into the larger tapered section 106 of the hole 102. There is a layer of semi-permanent adhesive 134 attached to the flat surface 112 of the bracket portion 110. This layer is protected by a release paper (not illustrated) until the assembly 68 is attached to the microscope 66. FIGS. 5A and 5B show the assembly 68 with the ribs 126 pointing down. This is clearly the preferred method of use because the ribs 126 will provide greater resistance to downward forces in this orientation. However, those familiar with the art to which this invention pertains will realize that the assembly 68 could be assembled and used with the ribs 126 pointing up.

The ophthalmic irrigation device 50, described above, is provided assembled and pre-sterilized, sealed in a pouch. A number of pouches and saline bags 90 are packed in each box or carton. To use the invention 50, a pouch is opened and the contents emptied aseptically. The saline bag 90 is suspended from an IV pole then the spike fitting 86 is attached to the bag 90. Using the roller control 94 all air is removed from the tube 78. The separation paper is removed from the adhesive 134 and the delivery unit adhered to the side of the microscope 66 in close proximity to the lens. The roller control 94 is adjusted so that the solution drips at a rate of one every 10–20 seconds. Finally, the cannula 54 is positioned so that desired irrigation is achieved by rotating and turning the ball 58. The invention 50 ready for use essentially illustrated in FIG. 1. During the operation, the position of the cannula and drip rate can be easily re-adjusted. After the operation, the entire assembly 50 is removed and discarded.

There are numerous advantages to using this invention 50:

it can be used in conjunction with any microscope;

the cannula 54 can be adjusted to irrigate any portion of the surgical arena;

a very steady mount for the delivery system 68 is provided the cannula 54 will not move during the operation;

the invention 50 is provided as a convenient, pre-sterilized kit; and the assembly 50 can be discarded after the operation is completed.

The pre-sterilized, disposable, ophthalmic irrigation device 50 has been described with reference to a particular embodiment. Other modifications and enhancements can be made without departing from the spirit and scope of the claims that follow.

What is claimed is:

1. An ophthalmic irrigation device for use in conjunction with a surgical microscope comprising:

a. a spike means for connection to a standard saline solution bag;

b. a cannula means for delivering saline solution to the surgical site;

c. a ball socket positioning means, through which said cannula means passes, for controlling positioning of said cannula means;

d. a bracket means, attached to said ball socket positioning means, for attaching said ball socket positioning means to said surgical microscope;

e. a tubular connection means for connecting said spike means to said cannula means; and f. a pressure means, positioned around said tubular connection means, for controlling the rate of flow of saline solution through said tubular connection means.

2. The irrigation device as claimed in claim 1 in which said cannula means has a slight curvature.

3. The ophthalmic irrigation device for use in conjunction with a surgical microscope comprising:

a. a ball having a diametrical through hole;

b. a cannula of length greater than the diameter of said ball, positioned and retained in said diametrical through hole;

c. a bracket having a vertical surface and an opposing horizontal rib;

d. a ring attached to said horizontal rib; said ring designed to accept and retain, approximately equatorially, said ball so that said cannula is kept in any desired position in relation to said ring by friction between said ring and said ball;

e. a layer of semi-permanent adhesive on said vertical surface which temporarily attaches said vertical surface to said surgical microscope;
f. means for protecting said layer of semi-permanent adhesive until it is desired to adhere said vertical surface to said microscope;
g. a length of tubing;
h. means for connecting to a standard saline solution bag at one end of said length of tubing;
i. means for connecting to said cannula at the other end of said length of tubing; and
j. means for controlling the rate of flow positioned around said length of tubing.

4. The irrigation device as claimed in claim 3 in which said cannula has a slight curvature.

5. The irrigation device as claimed in claim 3 in which said means for protecting said layer of semi-permanent adhesive is a release paper.

6. The irrigation device as claimed in claim 3 in which said means for controlling the rate of flow is a roller control.

7. A pre-sterilized, disposable ophthalmic irrigation kit for use in conjunction with a surgical microscope comprising:
    a. a bag of standard saline solution;
    b. a ball having a diametrical through hole;
    c. a cannula of length greater than the diameter of said ball, positioned and retained in said diametrical through hole;
    d. a bracket having a vertical surface and an opposing horizontal rib;
    e. a ring attached to said horizontal rib; said ring designed to accept and retain, approximately equatorially, said ball so that said cannula is kept in any desired position in relation to said ring by friction between said ring and said ball;
    f. a layer of semi-permanent adhesive on said vertical surface which temporarily attaches said vertical surface to said surgical microscope;
    g. means for protecting said layer of semi-permanent adhesive until it is desired to adhere said vertical surface to said microscope;
    h. a length of tubing;
    i. means for connecting one end of said length of tubing to said bag of standard saline solution bag;
    j. means for connecting the other end of said length of tubing to said cannula; and
    k. means for controlling the rate of flow positioned around said length of tubing.

8. The irrigation device as claimed in claim 7 in which said cannula has a slight curvature.

9. The irrigation device as claimed in claim 7 in which said means for protecting said layer of semi-permanent adhesive is a release paper.

10. The irrigation device as claimed in claim 7 in which said means for controlling the rate of flow is a roller control.

* * * * *